Figure 1:
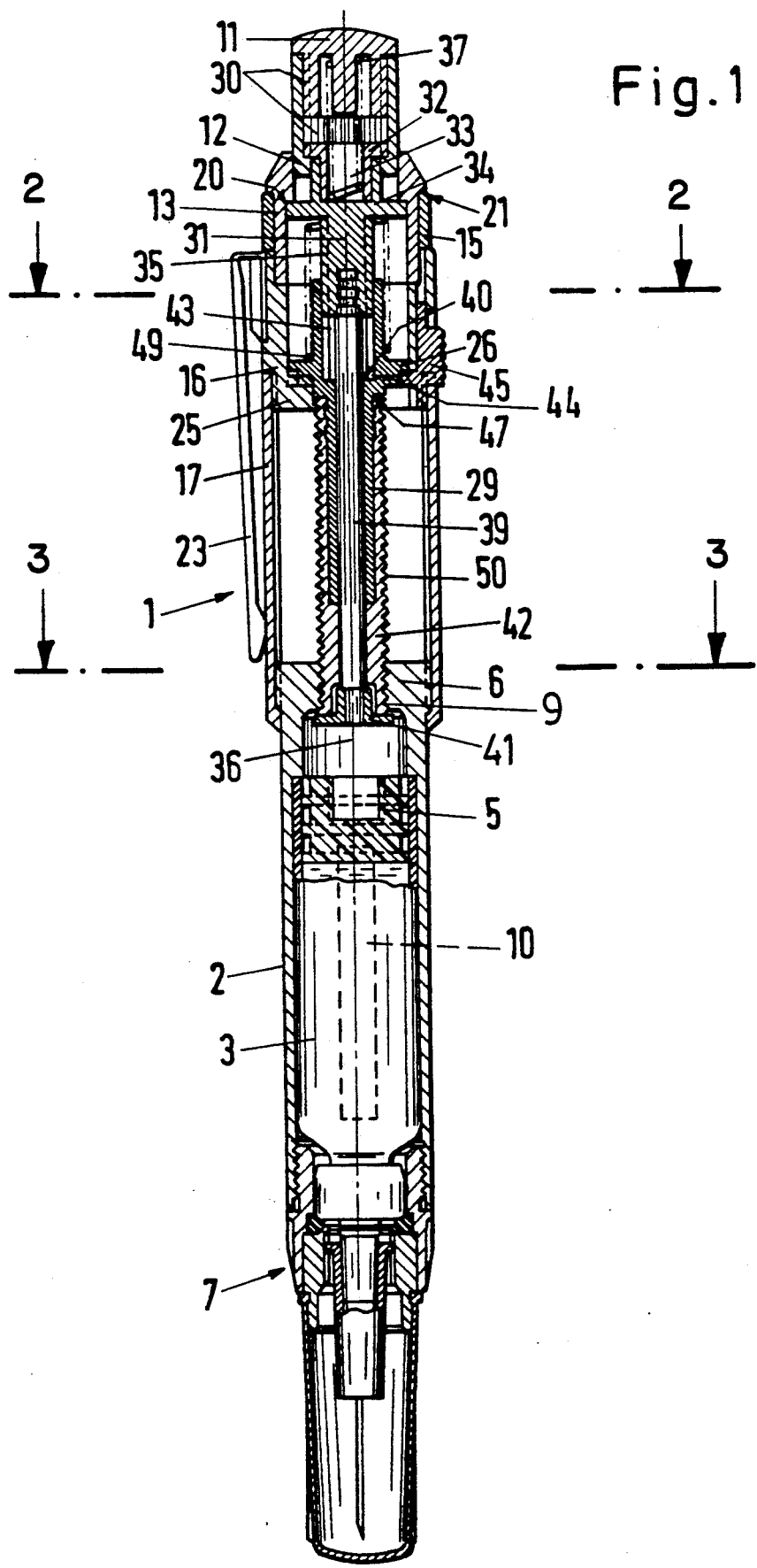

United States Patent [19]

Michel

[11] Patent Number: 5,112,317
[45] Date of Patent: May 12, 1992

[54] INJECTION DEVICE

[75] Inventor: Peter Michel, Burgdorf, Switzerland

[73] Assignee: Nosta Ag., Basel, Switzerland

[21] Appl. No.: 298,171

[22] Filed: Jan. 18, 1989

[30] Foreign Application Priority Data

Jan. 22, 1988 [CH] Switzerland ............ 00200/88

[51] Int. Cl.⁵ ............................................ A61M 5/24
[52] U.S. Cl. .................................. 604/208; 604/187;
604/232; 222/386
[58] Field of Search ............... 604/208, 211, 232, 209,
604/207, 210, 224, 218, 187, 110; 222/386, 390,
391

[56] References Cited

U.S. PATENT DOCUMENTS

| 792,299 | 6/1905 | Weaver | 604/224 |
|---|---|---|---|
| 2,283,915 | 5/1942 | Cole | 604/224 |
| 2,472,116 | 6/1949 | Maynes | 604/224 |
| 2,585,817 | 2/1952 | McLintock | 604/224 |
| 2,626,087 | 1/1953 | Howard et al. | 604/224 |
| 2,632,445 | 3/1953 | Kas | 604/209 |
| 2,660,342 | 11/1953 | Ruf | 604/224 |
| 2,706,480 | 4/1955 | Nensel | 604/211 |
| 3,905,366 | 9/1975 | Callahan et al. | 604/224 X |
| 4,112,945 | 9/1978 | Helixon et al. | 604/208 |
| 4,194,505 | 3/1980 | Schmitz | 604/211 X |
| 4,333,456 | 6/1982 | Webb | 604/232 |
| 4,413,760 | 11/1983 | Paton | 222/309 |
| 4,475,905 | 10/1984 | Himmelstrup | 604/208 |
| 4,561,856 | 12/1985 | Cochran | 604/143 |
| 4,581,022 | 4/1986 | Leonard et al. | 604/224 |
| 4,583,978 | 4/1986 | Porat et al. | 604/208 |
| 4,592,745 | 6/1986 | Rex et al. | 604/211 |
| 4,623,337 | 11/1986 | Maurice | 604/298 |
| 4,710,172 | 12/1987 | Jacklich et al. | 604/118 |
| 4,710,178 | 12/1987 | Leonard et al. | 604/209 |
| 4,865,591 | 9/1989 | Sams | 604/186 |
| 4,883,472 | 11/1989 | Michel | 604/208 |
| 4,936,833 | 6/1990 | Sams | 604/208 |
| 4,950,246 | 8/1990 | Muller | 604/218 |
| 4,968,299 | 11/1990 | Ahlstrand et al. | 604/224 |
| 4,973,318 | 11/1990 | Holm et al. | 604/208 |

FOREIGN PATENT DOCUMENTS

| 0219899 | 4/1987 | European Pat. Off. | 604/187 |
|---|---|---|---|
| 783520 | 7/1935 | France | 604/224 |
| 0250467 | 10/1987 | German Democratic Rep. | 604/187 |
| 8702895 | 5/1987 | World Int. Prop. O. | 604/187 |

Primary Examiner—C. Fred Rosenbaum
Assistant Examiner—Mark O. Polutta
Attorney, Agent, or Firm—Brady, O'Boyle & Gates

[57] ABSTRACT

A prefilled syringe (3) with plunger (5) is arranged in the lower housing member (2) of the injection device, and a drive stem (39) for the advancement of the plunger is supported in the upper housing member (1), this drive stem being advanceable by a specific stroke ($1_1$) by means of a knob (11) and being retractable by the same stroke ($1_1$) by means of a spring (49). The two housing members (1, 2) can be telescoped by means of a helical gear mechanism (9, 50) approximately by the entire advancement path ($1_3$) of the plunger (5) within the ampoule (3). The amount of fluid to be injected in each case is determined by the respective extent of telescoping of the two housing members (1, 2).

The length of the injection device is a measure for the content of the ampoule (3) so that the user, without giving special attention, will recognize when the liquid reservoir is running low by the feature that the device becomes increasingly shorter with progressive injections.

10 Claims, 3 Drawing Sheets

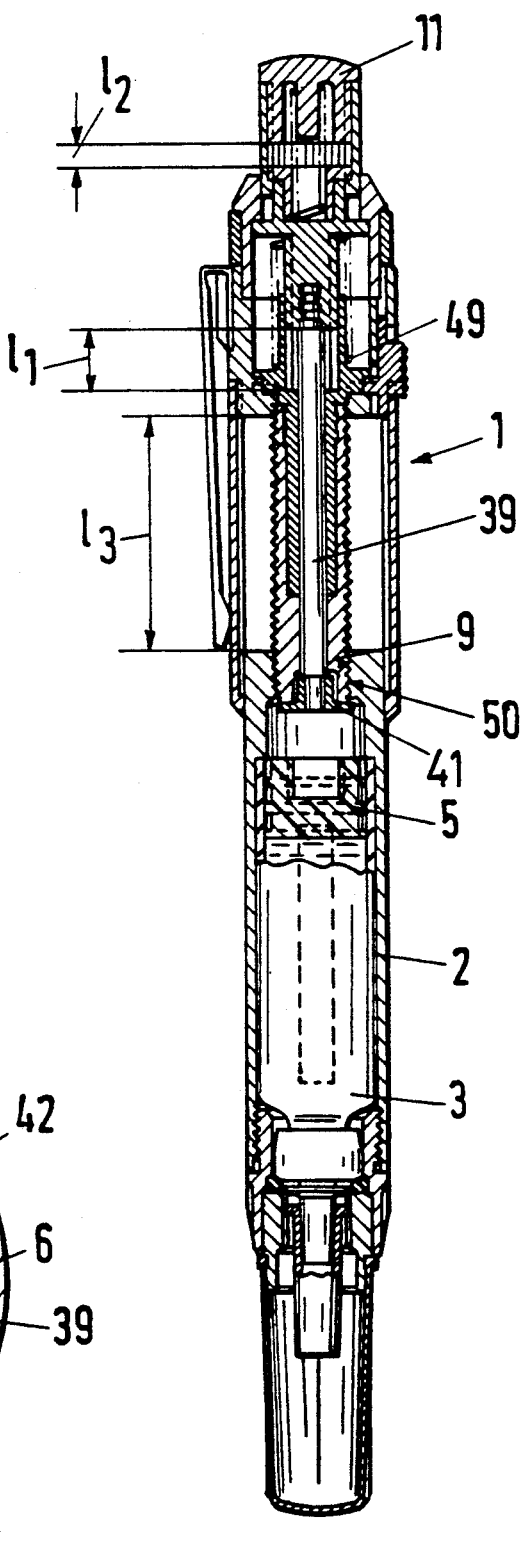
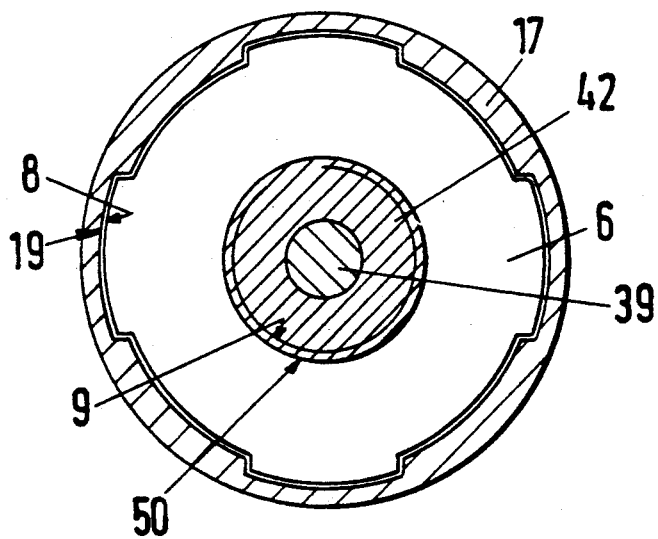

INJECTION DEVICE

The invention relates to an injection device.

A device of this type has been known from WO 87/02895. The drive stem for the advance of the plunger is a threaded rod forming the driven member of a gear mechanism and being threaded through a female thread of a gear element. The gear mechanism is supported to be able to reciprocate within the second housing member. The amount of fluid to be respectively injected is selected by appropriate rotation of the threaded rod by means of a knob constituting the drive member of the gear mechanism. The threaded rod is advanced by threading in correspondence with the rotation through the female thread of the gear element, this rod projecting to a continuously increasing extent into the ampoule with progression of the injection steps and being moved forwards and backwards together with the entire gear mechanism during each injection. The two housing members are detachably connected by threading via a threaded sleeve.

The injection device is intended for persons, e.g. diabetics, who must receive injections on a regular basis, in most cases several times a day. The device is usually employed by the patient himself and permits, with a single replaceable ampoule, a plurality of injections, for example all injections required within one week. Since the patient's well-being depends on injections that are to be performed regularly, there should be provided, in addition to easy handling, a readily recognizable indication of the ampoule content so that the patient will always carry along an adequate amount of injection fluid.

In the conventional injection devices, this is not the case. Although such devices have a window through which the ampoule and, if the latter is made of glass, also the plunger are visible, so that the fluid content level can basically be determined under sufficiently favorable light conditions, the recognition of a soon to be depleted fluid or fill level requires the patient's attention and good vision, which latter faculty is frequently absent precisely in such patients, so that there is the danger that the patient can no longer perform the necessary injection if he has failed to take a reserve ampoule along.

The invention is based on the object of providing a handy, simply operable injection device of the type discussed above, readily permitting an easy visual recognition of the fill level condition of the fluid reservoir by the patient.

The advantage attained by the invention is to be seen essentially in that the two housing members are continuously shifted with respect to each other in correspondence with the amount of fluid delivered in total from the liquid reservoir (ampoule) so that the total length of the injection device is constantly shortened with diminishing liquid reservoir. Therefore, the patient, in particular also the visually impaired patient, will ascertain without any special attentiveness, solely based on the decreasing total length of the device, whether the fluid in the container is running low. In order to determine with accuracy the fill level of the liquid container, a graduation can be arranged on the outside of the one housing member being covered by the other housing member, wherein the edge of the other housing member moving over the scale, or an indicator provided at this edge, shows the liquid or fill level. Furthermore, markings for the fill level that can be tactually felt by vision-impaired persons can be provided on the outside of one housing member, these markings being hidden by the other housing member in correspondence with the fill level.

In this connection, it is furthermore advantageous that the fill level can be estimated and/or can be determined from the graduation and, respectively, the markings even in case of an opaque fluid reservoir on the basis of the respective length of the device. (Opaque containers are required for radiation-sensitive [light-sensitive] fluids and can be utilized, for example, also for radioactive materials.)

Figure 2:
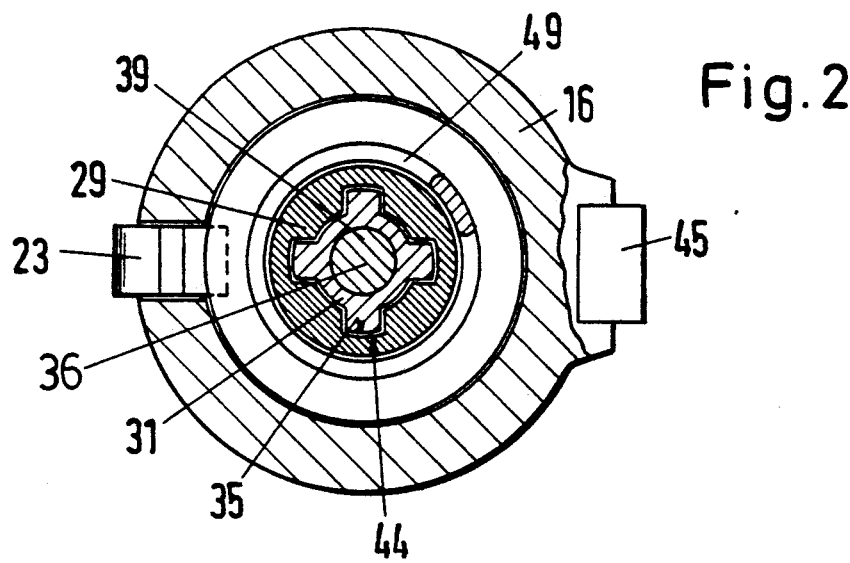
Figure 4:
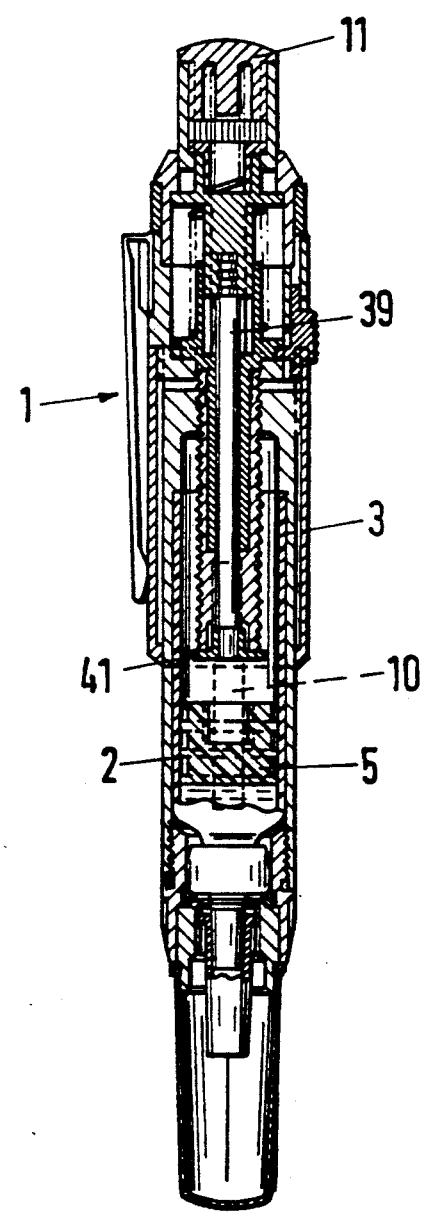

One embodiment of the invention will be described in greater detail below with reference to the drawings wherein:

FIG. 1 is a longitudinal section through an injection device wherein an ampoule is housed, prior to the first injection, FIG. 2 is a cross section along line 2—2 in FIG. 1, FIG. 3 is a cross section along line 3—3 in FIG. 1, FIG. 4 is a longitudinal section through the injection device after several injections, and FIG. 5 is a longitudinal section corresponding to FIG. 1 through the injection device, indicating the displacement paths.

The injection device illustrated in FIG. 1 comprises an upper housing member and a lower housing member 1 and 2. The lower housing member 2 is fashioned as a holder for an ampoule 3 (a so-called prefilled syringe or carpule) filled with the fluid to be injected; the ampoule is sealed at its top end by a plunger 5. The neck of the ampoule is inserted in a leakproof fashion in a needle holder 7 exchangeably locked in place at the lower end of the housing member 2 and being equipped with an injection needle. The lower housing member 2 exhibits along a surface line, in parallel to its axis, a narrow peephole 10 through which the position of plunger 5 can be observed. The upper end of member 2 has, as shown in sectional view in FIG. 3, an inwardly projecting annular shoulder 6 with an internal thread 9 and, on the outside, four splines 8.

The upper housing member 1 consists of a head section 13, an identification ring 15, a spacer element 16, and a sleeve 17 extending over the upper part of the lower housing member 2 and exhibiting grooves 19 on its inner wall wherein the splines 8 of the annular shoulder 6 are supported. Accordingly, the lower housing member 2 is secured nonrotationally in the upper housing member 1 and can be moved axially into the latter as will be described below.

In the bottom two-thirds, the inner wall of the head section 13 is offset by a step 20 toward the outside and the outer wall is offset by a step 21 toward the inside. Adjacent to the step 21, the recessed outer wall is covered to the extent of one-half by an identification ring 15. The identification ring 15 is labeled with information important to the patient. The spacer element 16 is seated on the bottom half of the recessed outer wall. The spacer element carries a clip 23 on the outside and an extension 25 on the inside at its lower end. The spacer element 16 is fixedly joined to the sleeve 17 forming the bottom portion of the upper housing member 1. The inner diameter of the sleeve 17 is larger by one tolerance than the outer diameter of the lower housing member 2.

A push button 11 forms the upper termination of the injection device; this push button comprises a tubular part extending at the bottom into the head section 13 and exhibiting at its lower, open end an annularly inwardly projecting extension 12 and, along its inner wall, axial guide splines 30 terminating at the extension 12.

An intermediate member 31 follows the push button 11, this member carrying at its upper end a collar 32 provided with grooves fitting together with the guide splines 30, as well as exhibiting an axial bore 33 extending approximately up to one-third into the intermediate member 31. At the level of the end of the bore 33, another collar 34 is provided on the outside of the intermediate member 31; axial longitudinal splines 35 extend below the collar 34 along the outside of the intermediate member up to the lower end of the latter. The collar 34 forms a stop for the extension 12 of the push button 11. The axis of the intermediate member 31 lies in the axis 36 of the injection device, and its collar 32 extends over the extension 12 of the push button 11. A spiral spring 37 is arranged in the axial bore 33 and continues into the cavity of the push button 11 and is clamped in place in between the bottom of the bore 33 and that of the head part of the push button 11. On account of the spring 37, the push button 11 and the intermediate member 31 are urged away from each other, the extension 12 of the push button 11 resting on the collar 32 of the intermediate member 31 in the inactivated condition.

A drive stem 39 lying in the axis 36 of the injection device is attached in the lower part of the intermediate member 31 and carries at its opposite end a disk 41. The drive stem 39 travels, with clearance fitting, in its upper part in a cylindrical driving sleeve 29 and in its lower part in a threaded sleeve 42.

The driving sleeve 29 exhibits in its upper third an axial bore 43 with axial longitudinal grooves 44 wherein the longitudinal splines 35 of the intermediate member 31 are in sliding engagement. The bottom 40 of the bore 43 constitutes a stop for the bottom end of the intermediate member 31. Below the upper third, the driving sleeve 29 has a collar 26 on its outer wall. A retaining spring 49 designed as a spiral spring urges, on the one hand, the collar 26 against the extension 25 and, on the other hand, the collar 34 against the step 20 of the head section 13. The spring constant of this spring is smaller than that of spring 37. The collar 26 and the annular extension 25 exhibit sawtooth-like locking elements permitting solely a rotation of the push button 11, non-rotationally connected with the driving sleeve 29 via the intermediate member 31, in the clockwise direction. Upon exchanging a consumed ampoule 3, the detent mechanism can be unlocked by an unlocking slide 45 lifting the collar 26 off the extension 25 against the bias of the spring 49 whereby backward rotation in the counterclockwise direction is made possible. Below the collar 26, the driving sleeve 29 has a step 47. The threaded sleeve 42 exhibiting an external thread 50 over its entire length is seated on the lower part of the driving sleeve 29 adjoining the step 47, this part having a smaller outer diameter than the upper part. The driving sleeve 29 and the threaded sleeve 42 are made up of two parts merely for assembly reasons and constitute a fixedly joined unit.

The mode of operation of the device will be described below with reference to FIG. 5 which shows, just as FIG. 1, the injection device prior to usage. A filled ampoule 3 with a plunger 5 arranged at the upper end is inserted in the bottom housing member 2, by pressing the needle holder 7 onto the ampoule neck and inserting the entire unit from the bottom into the housing member 2 with the plunger side of the ampoule 3 leading, until the needle holder 7 has been locked in place in the lower part of housing member 2. Subsequently, the injection device is held with the needle holder 7 pointing upwards, and pressure is exerted on the push button 11 up to the stop. Owing to the fact that the spring constant of the spring 37 is higher than that of the spring 49, the push button 11 is initially moved forwards with the intermediate member 31 against the bias of spring 49 by the stroke $l_1$. During this stroke $l_1$, the disk 41 of the drive stem 39, moved along with the intermediate member 31, abuts against the plunger 5 and urges the latter into the ampoule to such an extent that a small amount of liquid exits from the injection needle. At the end of stroke $l_1$, the forward end of the intermediate member 31 abuts against the bottom 40, but this is hardly noticed by the user since the push button 11 can be further moved against the force of the spring 37 by the stroke $l_2$ until the extension 12 abuts against the collar 34. During stroke $l_2$ the plunger 5 remains in its position. As soon as the push button 11 is released, the latter and the intermediate member 31 with the drive stem 39 return into the position illustrated in FIG. 5 under the action of the springs 37, 49. The plunger 5 is at this point spaced apart from the disk 41 exactly by the stroke $l_1$. For setting a desired injection volume, the push button 11 is rotated in the clockwise direction, the user perceiving a distinct clicking sound due to the locking elements at the extension 25 and collar 26. The number of clicks is a measure for the volume to be injected. The revolution of the push button 11 is transmitted via its longitudinal splines 30 and the grooves in the collar 32 to the intermediate member 31 and, from the latter (cf. FIG. 2) via its longitudinal splines 35 and the longitudinal grooves 44, to the driving sleeve 29 as well as the threaded sleeve 42 fixedly joined to the latter. The threaded sleeve engages with its thread 50 into the thread 9 of the annular shoulder 6 so that the lower housing member 2 is pulled into the upper housing member 1 in correspondence with the rotation of the push button 11 and thus in accordance with the volume to be injected. Consequently, the plunger 5 is now no longer spaced from the disk 41 by the stroke $l_1$ but rather by the stroke $l_1$ minus the (axial) distance $l_x$ by which the housing member 2 has been moved into the housing member 1 by the turning of the push button 11.

The needle is then inserted and the push button 11 pressed up to the stop. During this step, in the aforedescribed way, the drive stem 39 with the disk 41 is advanced by the stroke $l_1$. Injection begins at stroke $l_1$ minus adjusted displacement $l_x$ between upper and lower housing members 1 and 2 and is finished upon reaching the distance $l_1$ (abutment of the intermediate member 31 against the bottom 40), the push button 11, as mentioned above, being further urged by the path $l_2$ whereby it is ensured that the stroke $l_1$ is executed in its entirety and the whole injection volume set is applied. The lower housing member 2 can be pulled into the upper housing member 1 by rotation of the push button 11 by the distance $l_3$ in total until the annular shoulder 6 abuts against the extension 25. The distance $l_3$ (spacing of the annular shoulder 6, in the initial position shown in FIG. 1, from extension 25) is dimensioned to be of such a size that, on the one hand, the entire content of the ampoule (except for a small residual amount) can be injected and, on the other hand, it is ensured that the set injection volume can definitely be delivered, i.e. the plunger 5 cannot abut against the ampoule neck. Once the push button 11 can no longer be turned on account of abutting of the annular shoulder 6 against the extension 25, the user knows that the ampoule 3 is empty. With each injection, the injection device becomes a little shorter. The user can estimate the degree of fluid content of the ampoule 3 from the progressive shortening of the device.

The lower housing member 2 can be provided with a graduation extending along an outer surface line for the accurate fluid content level of the ampoule, the position of the lower edge of the sleeve 17 of the upper housing member 1 in each case indicating the fluid or fill level on the scale. In order to make the position of the lower edge of the sleeve 17, serving as an indicator, readily recognizable, this edge can be marked by coloring.

Furthermore, the lower housing member can be provided with indentations (or raised areas on the regions over which the grooves 19 travel) that can be felt by the vision-impaired, in order to indicate the fluid or fill level of the ampoule. For example, three peripheral grooves can be arranged for $\frac{3}{4}$ full, a pair of peripheral grooves for $\frac{1}{2}$ full, and one peripheral groove for $\frac{1}{4}$ full, in such a way that the bottom edge of the sleeve 17 is located at the respective peripheral groove arrangement when the respective fluid level has been reached, and covers such arrangement once the level has fallen below this value.

Additionally to or in place of the aforementioned graduation and/or raised areas or indentations, a tactually perceivable minimum warning marker can further be provided, arranged in such a way that it is covered by the edge of the sleeve 17 once a minimum fluid level condition permitting at this point only a few more injections, e.g. only injections for a single day's need, has been reached. The user, especially also the vision-impaired user, then can reliably perceive in all instances whether the fluid level is still adequate for the respective day or whether the ampoule must be replaced. Indication of the fluid content level can also take place, instead of using the edge of the sleeve 17, by means of an indicator arranged at the sleeve, or by a marking in a window at the lower edge of the sleeve 17.

In order to exchange the ampoule, the needle holder 7 with the consumed ampoule is removed and, with the unlocking sleeve 45 having been urged upwardly, the push button 11 is turned back in the counterclockwise direction until the housing member 2 has again been advanced into the position illustrated in FIG. 1 (and FIG. 5). (The threaded sleeve 42 is designed at its lower end so that further turning past the position indicated in FIG. 1 is impossible.)

The injection device can also be designed merely with a drive stem that can be reciprocated in the upper housing member by a stroke predetermined by means of stops, this drive stem projecting at the top out of the housing member and being urged downwardly directly by hand against the bias of a spring. For setting the injection volume, one of the two housing members can be equipped with an outer thread and the other with an inner thread so that the two housing members can be inserted one in the other by threading.

I claim:

1. A device for delivering a plurality of preselected doses of a liquid drug from a loaded liquid reservoir (3), co-axially abutting against a plunger (5) at its upper end and a needle holder (7) at its lower end, having a first housing member (2) to accommodate the liquid reservoir (3) and a second housing member (1) coaxially and telescopically movably connected relative to the first housing member (2), and a drive stem (39) connected on the axis (36) of the device for reciprocal movement forward and backward exclusively by the same stroke distance $l_1$ moveable into contact with the plunger (5) to cause the plunger (5) to advance to deliver doses of liquid from the liquid reservoir through the needle holder, the improvement comprising:

means (11, 30, 32, 31, 35, 44, 29, 42, 50,) connected in said second housing member (1) and connected (9, 50, 25, 26) for rotative movement to both said first and second housing members (2, 1) to move the first and second housing members (2, 1) into each other by a selectable axial path $l_x$;

said means including push button means (11, 30, 32, 31) connected for reciprocal movement in said second housing member (1) and said means (11, 30, 32, 31, 35, 66, 29, 42, 50) and having a portion (11, 30) projecting from said second housing member (1);

said drive stem (39) connected at one end to said push button means (11, 30, 32, 31) and connected for reciprocal movement in said means (11, 30, 32, 31, 35, 44, 29, 42 50) to position the opposite end (41) of said drive stem (39) relative to the plunger (5) at an axial distance corresponding to the stroke path $l_1$, and the opposite end (41) of said drive stem (39) extending from said means (11, 30, 32, 31, 35, 44, 29, 42, 50) into said first housing member (2) adjacent said plunger 5, whereby rotation of said means (11, 30, 32, 31, 35, 44, 29, 42, 50) by said push button means (11) by a selected amount moves said first housing member (2) into said second housing member (1) by a selected axial distance $l_x$ corresponding to the selected dose to be delivered thereby reducing the preset axial distance $l_1$ between said opposite end (41) of the drive stem (39) and the plunger (5) to $l_1 - l_x$ and causing the plunger (5) to be axially advanced by the amount of $l_x$ only upon reciprocally moving the drive stem (39) along its stroke path $l_1$ by said push button means (11).

2. A device according to claim 1, in which the plunger (5) has an advancing path distance $l_3$ within the liquid reservoir (3), and said first and second housing members (2, 1) are moveable into each other by said means by at least approximately the entire advancing path distance $l_3$ of the plunger (5) within the liquid reservoir (3).

3. A device according to claim 1, in which said means includes a helical gear mechanism (9, 50) connected between the first and second housing members (2, 1), whereby the first and second housing members are telescopically moveable into each other.

4. A device according to claim 1, including guide means (8, 19) connected between the first and second housing members (2, 1) to prevent relative rotation between the first and second housing members.

5. A device according to claim 3, in which said helical gear mechanism (9, 50) includes a rotatable helically threaded sleeve (29, 42), said drive stem (39) coaxially connected for longitudinally displaceable movement within said rotatable sleeve (29, 42), said portion (11, 30) of said push button means (11, 30, 32, 31) projecting from said second housing member on the end opposite from said first housing member (2), spring means (49) connected between said push button means (11) and said rotatable sleeve (29, 42), said push button means (11) connected to said drive stem (39) to longitudinally move said drive stem (39) within said rotatable sleeve (29, 42) against the bias of said spring means (49), and said push button means (11) coupled to said rotatable sleeve (29, 42), whereby rotation of said push button means (11) rotates said rotatable helically threaded sleeve (29, 42).

6. A device according to claim 4, in which said means includes a rotatable helically threaded sleeve (29, 42) connected between said first and second housing members (2, 1), said drive stem (39) coaxially connected for longitudinally displaceable movement within said rotatable sleeve (29, 42), said portion (11, 30) of said push button means (11, 30, 32, 31) projecting from said second housing member on the end opposite from said first housing member (2), spring means (49) connected between said push button means (11) and said rotatable sleeve (29, 42), said push button means (11) connected to said drive stem (39) to longitudinally move said drive stem (39) within said rotatable sleeve (29, 42) against the bias of said spring means (49), and said push button means (11) coupled to said rotatable sleeve (29, 42), whereby rotation of said push button means (11) rotates said rotatable helically threaded sleeve (29, 42).

7. A device according to claim 5, in which said helical gear mechanism (9, 50) includes an internal thread (9) on the end (6) of said first housing member (2) facing said second housing member (1), and said rotatable helically threaded sleeve (29, 42) having an external thread (50) cooperating with said internal thread (9) on the end (6) of said first housing member (2) facing said second housing member (1).

8. A device according to claim 1, including graduation markings indicative of the level of the liquid in the liquid reservoir (3) provided on the outside of said first housing member (2), and said second housing member (1) being telescopically moveable over said graduation markings.

9. A device according to claim 1, including tactual markings indicative of the liquid level of the liquid in the liquid reservoir (3) provided on the outside of said first housing member (2), and said second housing member (1) being telescopically moveable over said tactual markings.

10. A device according to claim 1, wherein the liquid reservoir (3) is a prefilled syringe, preferably of the ampoule type.

* * * * *